(12) United States Patent
Powers et al.

(10) Patent No.: US 7,373,802 B2
(45) Date of Patent: May 20, 2008

(54) TESTING FIXTURE AND METHOD FOR DETERMINING TOUGHNESS OF MOLDED PLASTIC COMPONENTS

(75) Inventors: Rodney G. Powers, Gainesville, FL (US); Robert M. Langley, Hawthorne, FL (US)

(73) Assignee: The State of Florida, Department of Transportation, Tallahassee, FL (US)

( * ) Notice: Subject to any disclaimer, the term of this patent is extended or adjusted under 35 U.S.C. 154(b) by 121 days.

(21) Appl. No.: 11/498,552

(22) Filed: Aug. 3, 2006

(65) Prior Publication Data

US 2008/0028825 A1 Feb. 7, 2008

(51) Int. Cl.
*G01M 19/00* (2006.01)

(52) U.S. Cl. .................. 73/12.09; 73/12.04; 73/12.06; 73/12.11; 73/12.12; 73/12.13; 73/78

(58) Field of Classification Search .............. 73/12.04, 73/12.06, 12.09, 12.11, 12.12, 12.13, 78
See application file for complete search history.

(56) References Cited

U.S. PATENT DOCUMENTS

| | | | |
|---|---|---|---|
| 3,359,792 A | | 12/1967 | Lukens |
| 3,380,289 A | | 4/1968 | Walters |
| 4,531,400 A | * | 7/1985 | Nevel ........................ 73/12.13 |
| 5,191,783 A | | 3/1993 | Abbott |
| 5,214,954 A | | 6/1993 | Abbott |
| 5,457,984 A | * | 10/1995 | Ambur et al. ............. 73/12.09 |
| 5,739,411 A | | 4/1998 | Lee |
| 5,959,198 A | * | 9/1999 | Pollok et al. .................. 73/79 |
| 6,523,391 B1 | | 2/2003 | Knox |
| 6,807,841 B1 | * | 10/2004 | Chen et al. ................ 73/12.06 |
| 6,848,293 B2 | | 2/2005 | DeRuiter |

* cited by examiner

*Primary Examiner*—Edward Lefkowitz
*Assistant Examiner*—Freddie Kirkland, III
(74) *Attorney, Agent, or Firm*—J. Wiley Horton

(57) ABSTRACT

A method and testing fixture for toughness-testing corrugated high density polyethylene (HDPE) pipe. The method includes the steps of preparing a test sample, attaching the test sample in the testing fixture, and providing an impact load to the test sample. The test sample is cut from a section of corrugated HDPE pipe so as to have a clamped portion and a loading member extending outwardly therefrom. The clamped portion includes two sidewalls with a trough therebetween. A hole is bored in the loading member near the end of the loading member. The testing fixture includes a vertical clamp which is configured to grip the clamped portion of the test sample so as to retain the clamped portion in a stationary position when the test sample is loaded. The loading member of the test sample projects outwardly from the vertical clamp. A guide rod is attached to the loading member through the bore in the loading member. One or more masses are slidably situated on the guide rod so that they can fall from a first position to a second position. A stop collar is attached near the second end of the guide rod to arrest the freefall of the masses, causing an impact load to be transmitted up the guide rod to the loading member.

15 Claims, 8 Drawing Sheets

TESTING FIXTURE AND METHOD FOR DETERMINING TOUGHNESS OF MOLDED PLASTIC COMPONENTS

BACKGROUND OF THE INVENTION

1. Field of the Invention

This invention relates to the field of materials testing. More specifically, the present invention comprises a method and apparatus for toughness-testing corrugated high density polyethylene pipe.

2. Description of the Related Art

Corrugated high density polyethylene ("HDPE") pipe is commonly used in many drainage applications. For example, corrugated HDPE pipe is widely used in highway drainage systems, storm water diversion and retention systems, agricultural drainage systems, and on-site wastewater systems. Corrugated HDPE pipe is a popular piping option because it is durable, flexible, lightweight, cheap and easy to install. HDPE is a relatively inert plastic and is resistant to mechanical abrasion. Because of its corrugated construction, corrugated HDPE pipe is also capable of withstanding many static and dynamic loading conditions. It has been used as a replacement for concrete pipe in many applications.

Corrugated HDPE pipe is also widely popular because it is easy to size and install. The pipe may be obtained in long lengths from the manufacturer. When smaller lengths are needed, it can easily be cut to any desired length. For applications where longer lengths of piping is needed, corrugated HDPE pipes can be effectively coupled together to create a water-tight and silt-tight seal.

Corrugated HDPE pipe has several common modes of failure. One commonly observed mode of failure involves "cracking" along corrugation fold lines under static or dynamic loading conditions. Cracking failures may be reduced by quality control. Although various testing procedures are generally available for strength-testing materials, none of the prior art methods are effective for evaluating the effect of static and dynamic loading conditions on corrugation fold lines. Thus, it is advantageous to provide a testing method specifically designed to evaluate the corrugation fold lines.

BRIEF SUMMARY OF THE INVENTION

The present invention comprises a method and testing fixture for strength-testing corrugated high density polyethylene (HDPE) pipe. The method includes the steps of preparing a test sample, attaching the test sample in the testing fixture, and providing an impact load to the test sample. The test sample is cut from a section of corrugated HDPE pipe so as to have a clamped portion and a loading member extending outwardly therefrom. The clamped portion includes two sidewalls with a trough therebetween. A hole is bored in the loading member near the end of the loading member.

The testing fixture includes a vertical clamp which is configured to grip the clamped portion of the test sample so as to retain the clamped portion in a stationary position when the test sample is loaded. The loading member of the test sample projects outwardly from the vertical clamp. A guide rod is attached to the loading member through the bore in the loading member. In the preferred embodiment one end of the guide rod attaches to the loading member with an attachment knob. One or more masses or weights are slidably situated on the guide rod. In the preferred embodiment the masses are held in place at a first position on the guide rod by a plunger. When the plunger is pulled, the masses are released and fall to a second position on the guide rod. A stop collar is attached near the second end of the guide rod to arrest the freefall of the masses, causing an impact load to be transmitted up the guide rod to the loading member.

Figure 1:
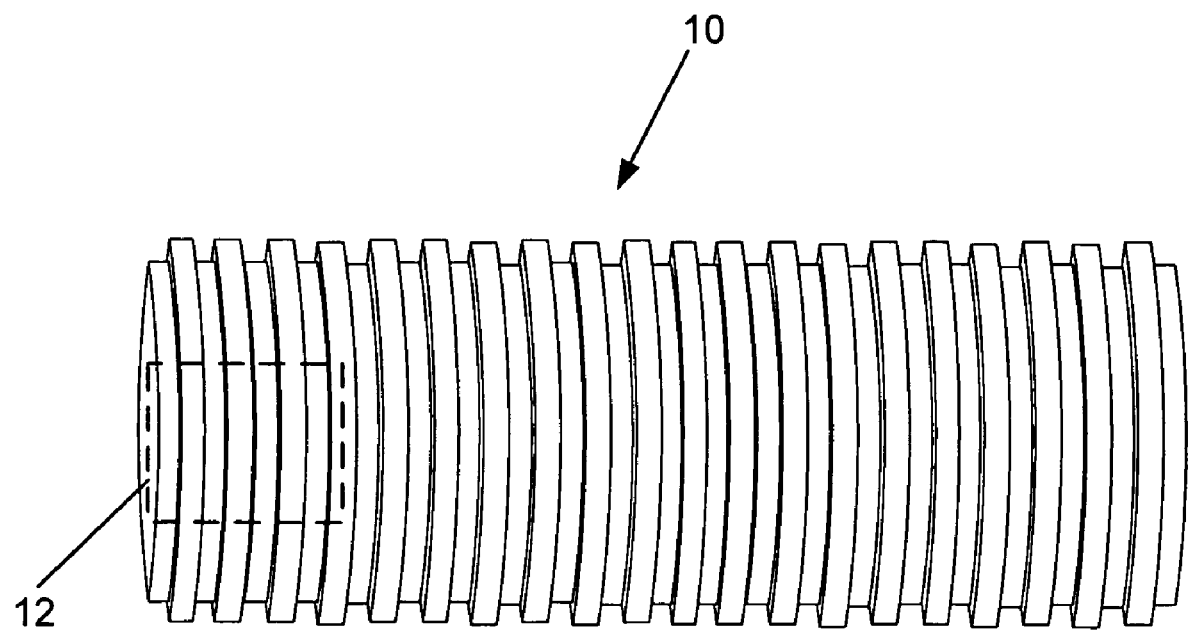
FIG. 1 is a perspective view, showing a length of corrugated HDPE pipe.

| REFERENCE NUMERALS IN THE DRAWINGS | | | |
|---|---|---|---|
| 10 | pipe | 12 | section |
| 14 | peaks | 16 | troughs |
| 18 | test sample | 20 | sample section |
| 22 | stress concentration zone | 24 | loading member |
| 26 | bore | 28 | sidewall |
| 30 | sidewall | 32 | valley |
| 34 | testing fixture | 36 | vertical clamp |
| 38 | knob | 40 | screw |
| 42 | clamp face | 44 | slot |
| 46 | knob | 48 | male thread |
| 50 | support brace | 52 | weights |
| 54 | plunger | 56 | guide rod |
| 58 | stop collar | 60 | screw receiver |
| 62 | screw receiver | 64 | sidewall mating surface |
| 66 | vertical clamp slot | 68 | plunger receiver |
| 70 | sleeve | 72 | test sample |
| 74 | clamp | 76 | clamp |
| 78 | rod receiver | 80 | stop plate |
| 82 | dampers | 84 | brace |

DETAILED DESCRIPTION OF THE INVENTION

Figure 2:
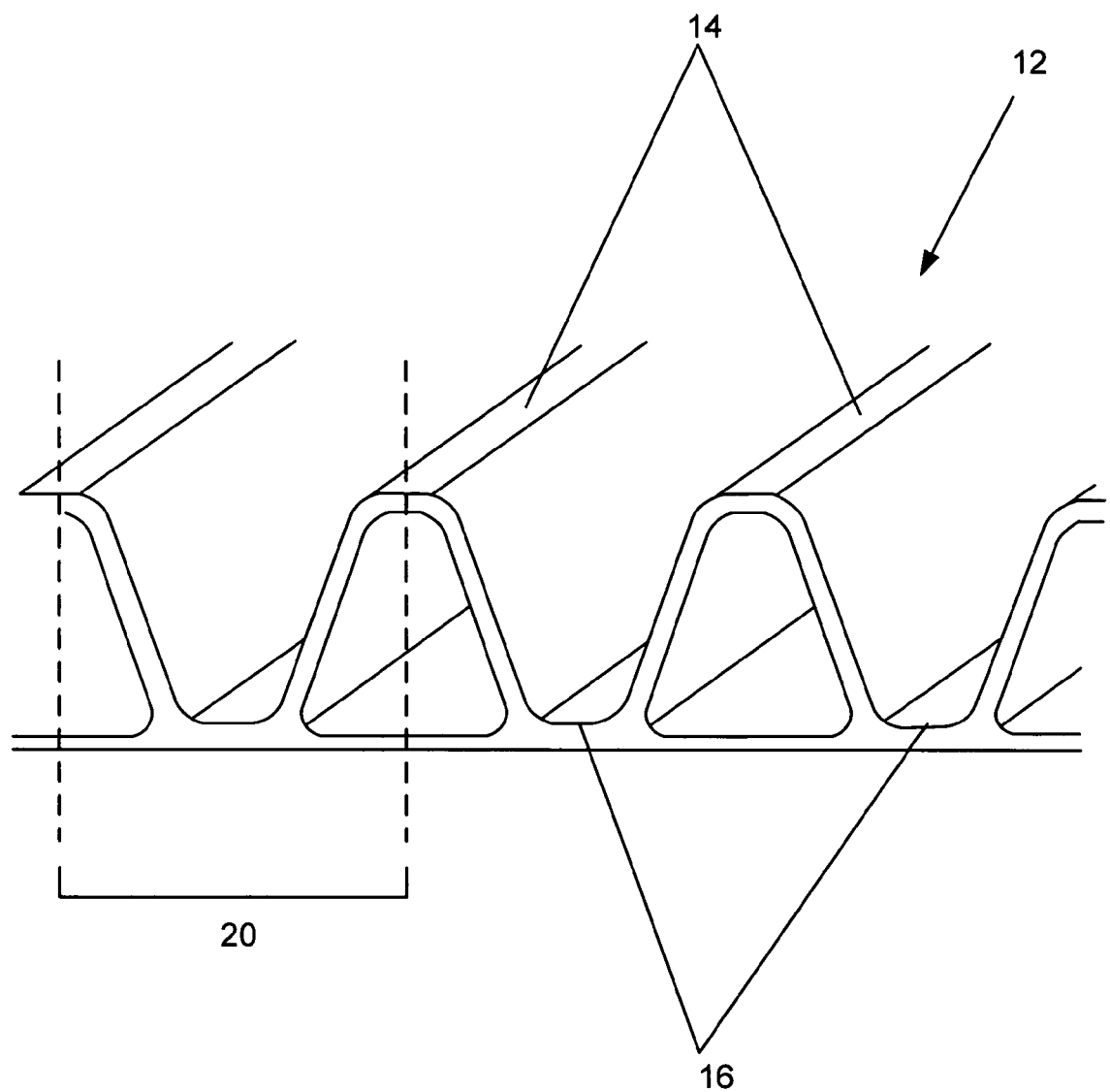
FIG. 2 is a perspective view, showing a section of corrugated HDPE pipe.

The present invention comprises a method and testing fixture for strength-testing corrugated high density polyethylene (HDPE) pipe. A length of corrugated HDPE is illustrated in FIG. 1 as pipe 10. Section 12 of pipe 10 in FIG. 1 is cut and removed from pipe 10 and illustrated in FIG. 2. The reader will note that the series of corrugation fold lines creates alternating peaks 14 and troughs 16. Some corrugated HDPE pipe does not have actual fold lines. Instead, some employ an undulating curved surface. Although not as angular, these varieties of HDPE pipe also have alternating peaks and troughs. For the purposes of the present invention a single sample section 20 is needed to prepare test sample 18 (illustrated in FIG. 3). Although the testing method is described for a single sample section 20, many runs of the testing method generally must be performed on many different sample sections to obtain statistically useful data.

Figure 3:
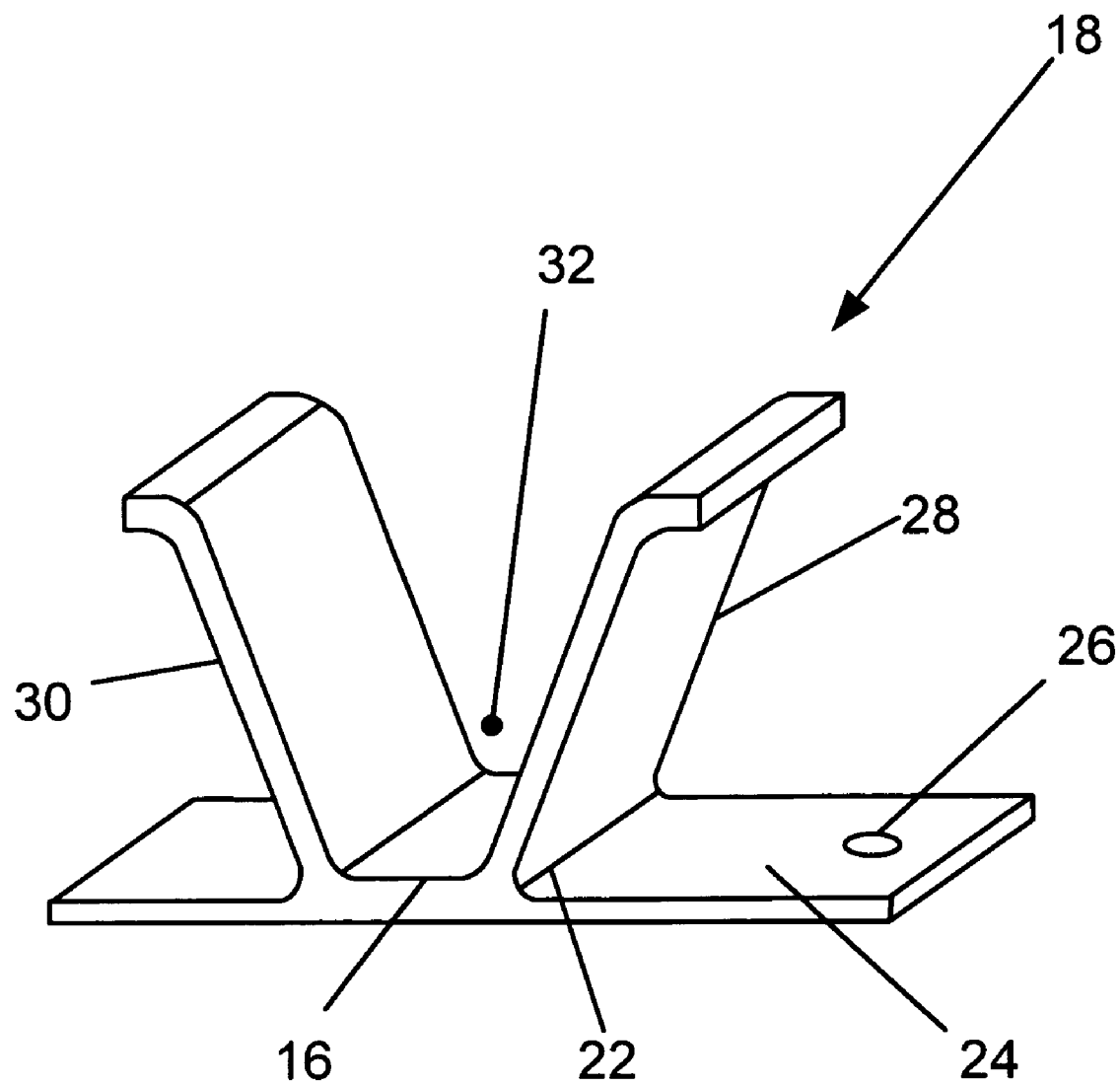
FIG. 3 is a perspective view, showing a test sample used in the present invention.

A prepared test sample is illustrated in FIG. 3. Test sample 18 was cut from a section of corrugated HDPE pipe. Test sample 18 is cut from section 12 so that it has sidewall 30, sidewall 28, and trough 16 therebetween. This portion of test sample 18 is referenced as the "clamped portion" since the clamp of the testing fixture inserts into valley 32 between sidewall 30 and sidewall 28 and mates with sidewall 30, sidewall 28, and trough 16. Loading member 24 extends outwardly from the clamped section from sidewall 28. Bore 26 is drilled through one end of loading member 24.

It has been observed that corrugated HDPE pipe often fails at the corrugation fold lines, indicated by stress concentration zone 22 in FIG. 3. The proposed testing method and testing fixture is designed to expose test sample 18 to loading conditions, particularly impulse loading conditions, which concentrate stress in concentration zone 22 between sidewall 28 and loading member 24. Those that are skilled in the art know that various devices can be used to measure stress, strain, and deformation of components of test sample 18. The types of analyses that may be performed on test sample 18 using the proposed testing method and testing fixture are beyond the scope of the present invention, however.

Figure 4:
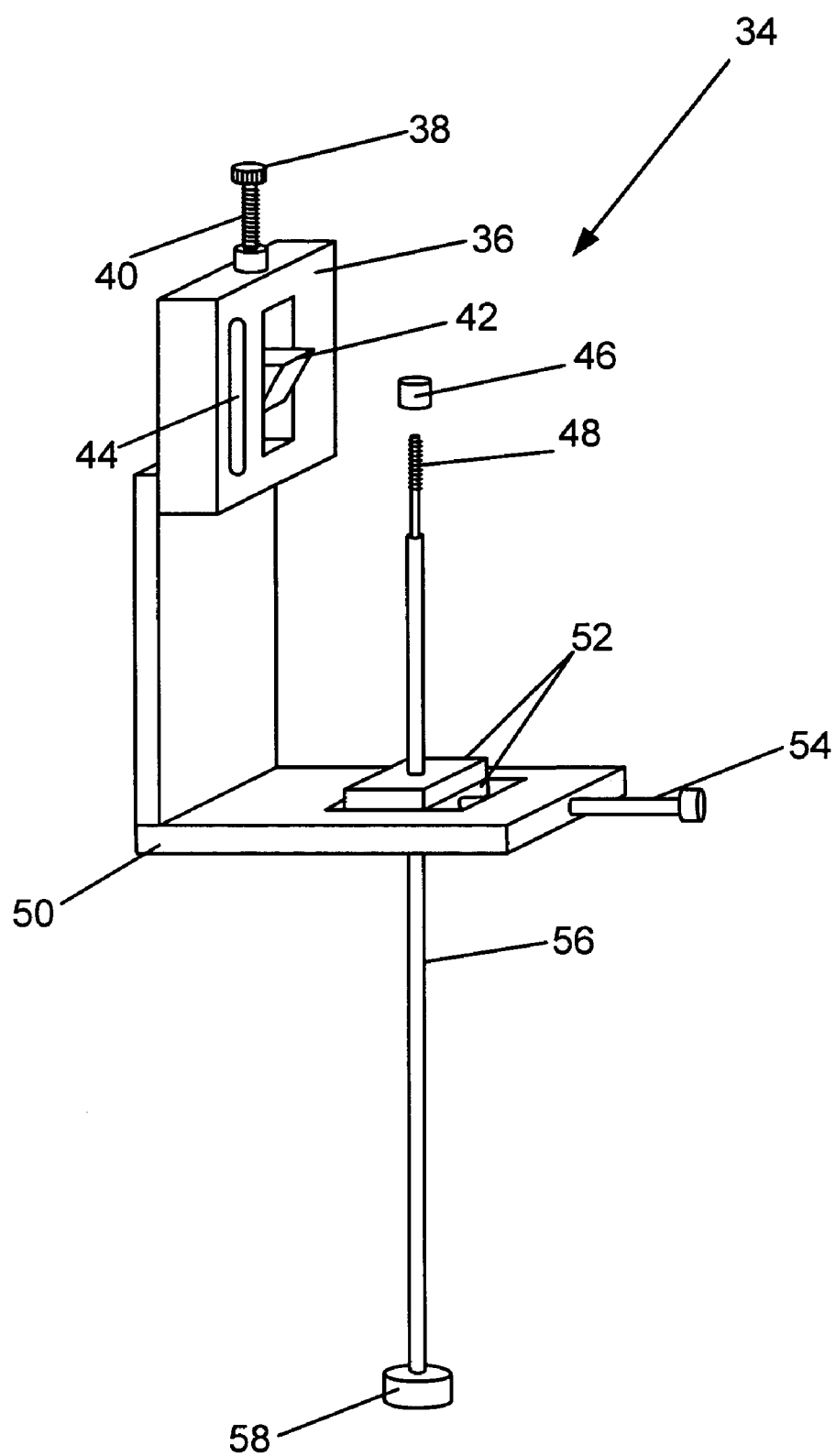
FIG. 4 is a perspective view, showing a testing fixture.

FIG. 4 shows testing fixture 34, which may be used to test and analyze the effects of various loading conditions on test sample 18. Testing fixture 34 includes a vertical clamp 36 which is configured to grip the clamped portion of test sample 18 so as to retain the clamped portion in a stationary position when the test sample 18 is loaded. Vertical clamp 36 includes screw 40 which moves clamp face 42 up and down. Knob 38 is provided for turning screw 40. Support brace 50 holds vertical clamp 36 in a fixed position. Support brace 50 may be attached to a table top or to any other supportive structure or clamped in a vice.

Guide rod 56 is provided for transmitting the load to the loading member of the test sample. Male thread 48 is provided on one end of guide rod 56 for attaching guide rod 56 to the test sample. Knob 46 has a female thread (not shown) which is configured to engage male thread 48 when the two components are threadedly connected. Stop collar 58 is removably fastened to guide rod 56 at the other end. Stop collar 58 is preferably adjustably fastened in such a manner that stop collar 58 may be attached at various locations along the length of guide rod 56. Weights 52 are slidably situated on guide rod 56 such that weights 52 may move up and down along the length of guide rod 56. In the preferred embodiment, a hole is provided through the center of weights 52. Guide rod 56 is inserted through this hole before guide rod 56 is attached to the test sample. Because the holes are smaller in diameter than stop collar 58, weights 52 cannot pass over stop collar 58 when the weights are released.

Figure 7:
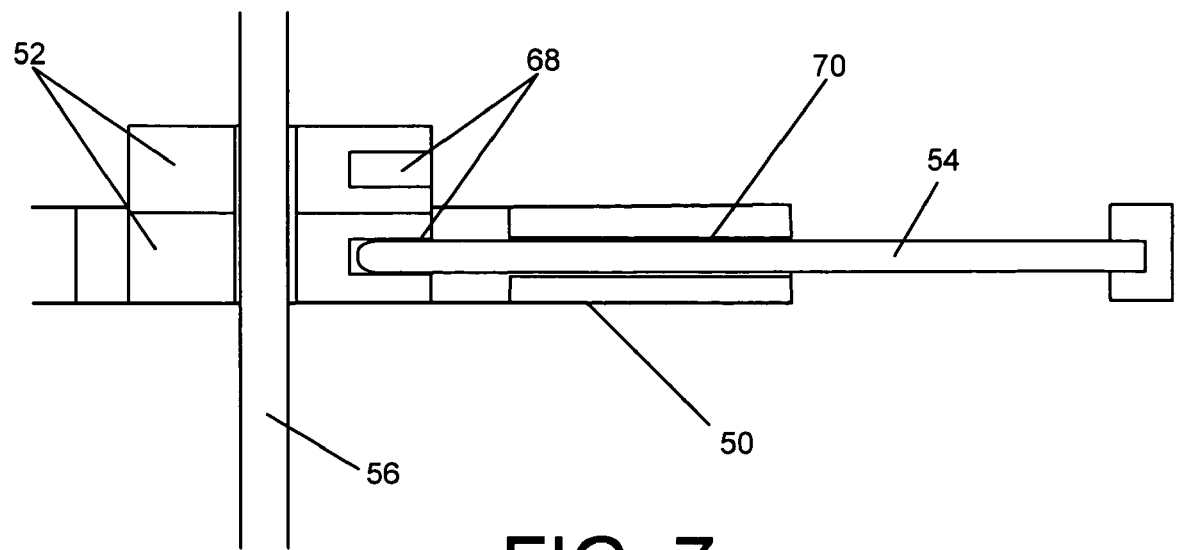
FIG. 7 is a section view, showing the mechanical engagement of the plunger and weights.

As illustrated in FIG. 7, weights 52 are held in place at a first position on guide rod 56 by plunger 54. Plunger 54 inserts through sleeve 70 in support brace 50 and into plunger receiver 68 in the bottom weight or mass. When the plunger 54 is pulled, weights 52 are released and fall to a second position on guide rod 56. Stop collar 58 arrests the freefall of weights 52, causing an impact load to be transmitted up guide rod 56 to the loading member. Thus, the position of stop collar 58 on guide rod 56 marks the second position.

Figure 5:
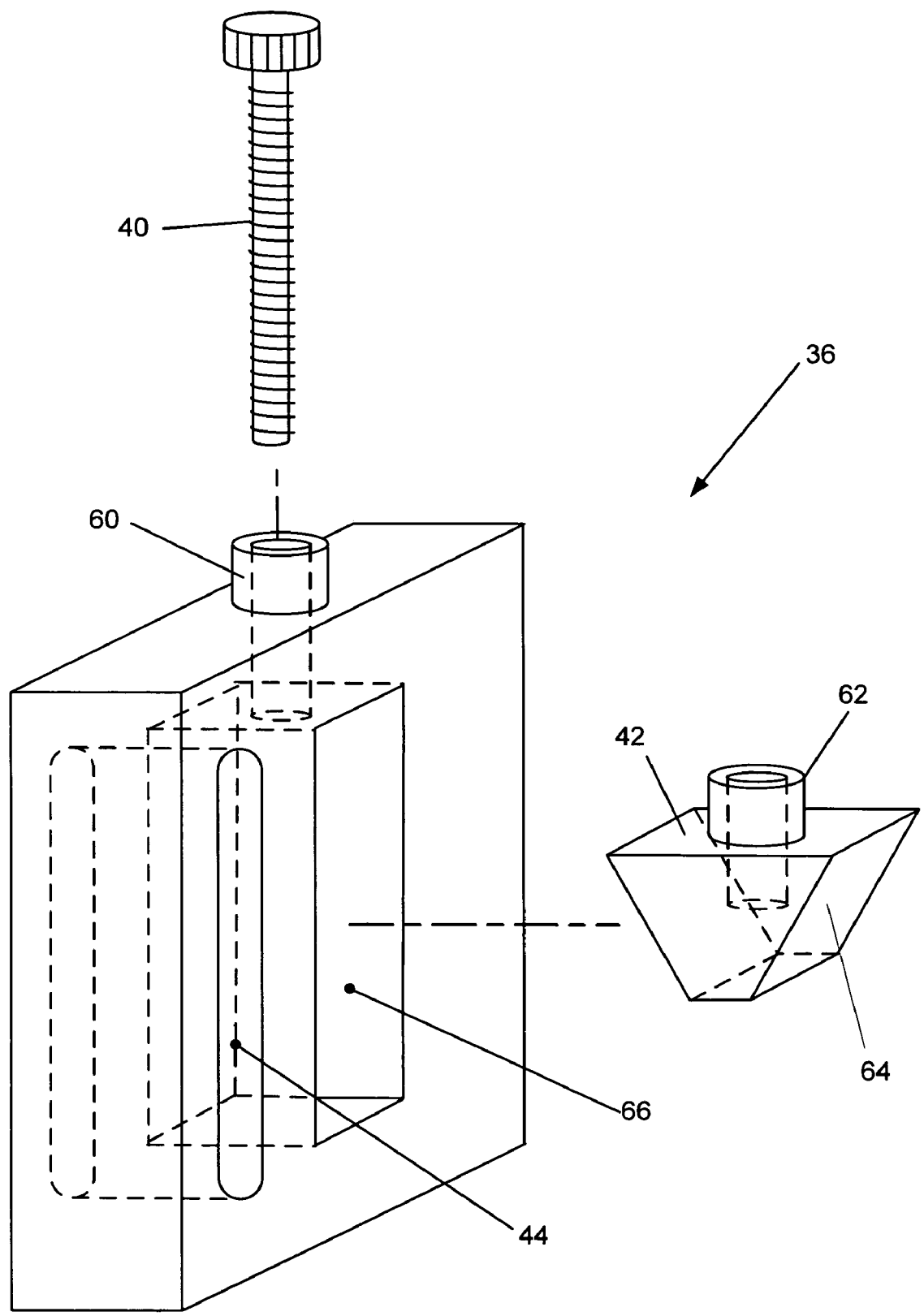
FIG. 5 is an exploded view, showing a vertical clamp.

Vertical clamp 36 is shown in greater detail in FIG. 5. Screw 40 engages screw receiver 60 of vertical clamp 36 so that one end of screw 40 projects into vertical clamp slot 66 and into screw receiver 62 of clamp face 42. When screw 40 is rotated clamp face 42 moves up or down within vertical clamp slot 66. Clamp face 42 includes a pair of sidewall mating surfaces 64 (One sidewall mating surface faces away from the viewer in FIG. 5 on the opposite side of clamp face 42 from sidewall mating surface 64). Slot 44 is provided parallel to vertical clamp slot 66. Slot 44 may be used when employing a horizontal clamp. For example, a c-clamp may be placed through slot 44 so that the clamp presses the sidewalls of the test sample against sidewall mating surfaces 64.

Figure 6:
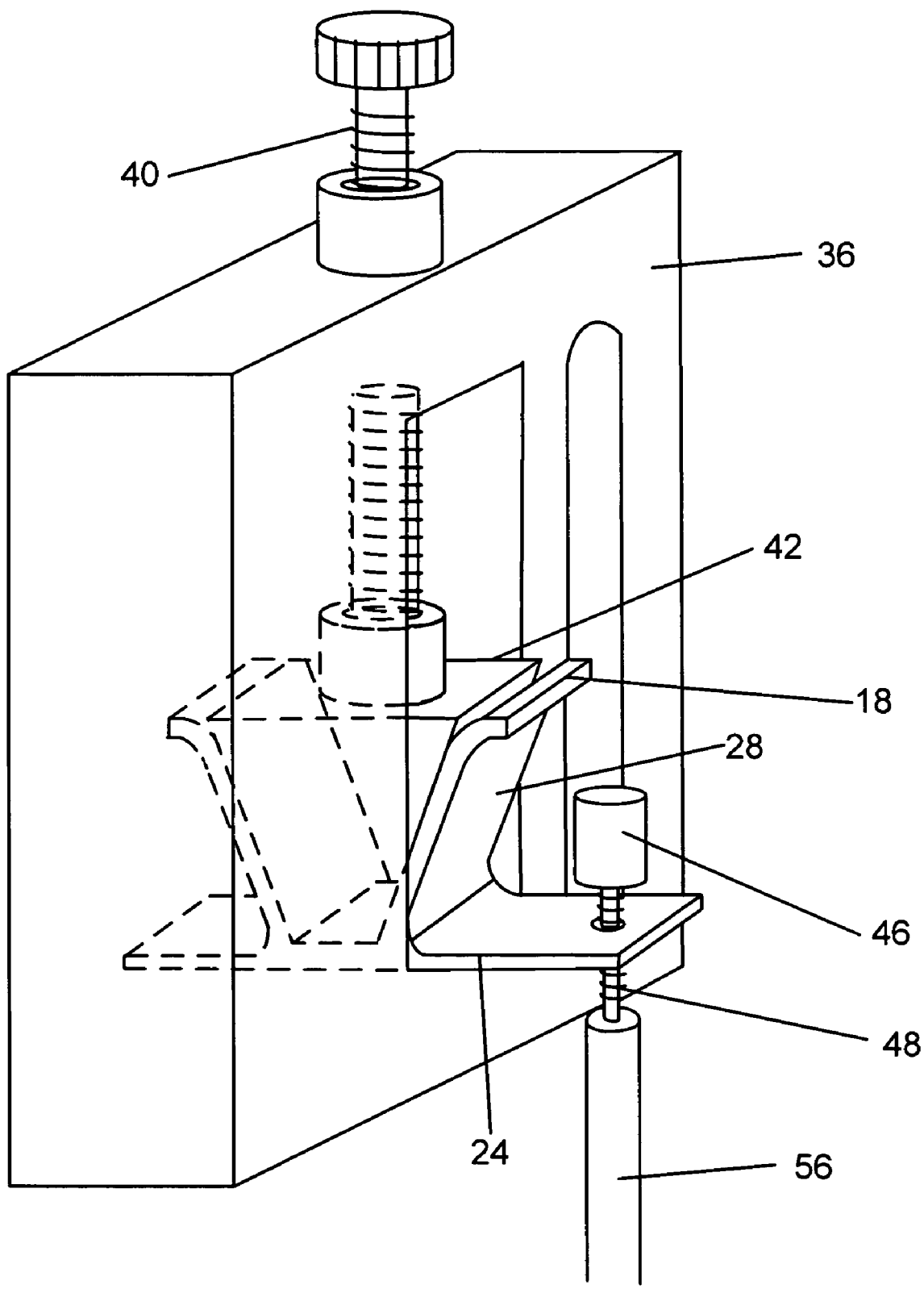
FIG. 6 is a perspective view with hidden lines, showing the present invention.

FIG. 6 illustrates how test sample 18 may be attached to the testing fixture. The clamped portion of test sample 18 is placed beneath clamp face 42 so that clamp face 42 is above valley 32. Screw 40 is then used to tighten clamp face 42 against the clamped portion of test sample 18. When clamp face 42 is clamped against trough 16, sidewalls 28 mate with sidewall mating surfaces 64. When test sample 18 is clamped in this orientation, loading member 24 projects outwardly away from vertical clamp 36.

Guide rod 56 is then attached to test sample 18. Male thread 48 is inserted through bore 26 of loading member 24. Knob 46 is then attached to the end of guide rod 56 by threadedly engaging the female thread on knob 46 with male thread 48 and tightened. Once the "clamped portion" of test sample 18 is clamped into vertical clamp 36 and guide rod 56 is attached to loading member 24, the tester may attach various analyses devices to test sample 18 or testing fixture 34, including strain gauges and other devices suitable for measuring deflection or deformation. Test sample 18 is subjected to an impact load by pulling plunger 54 which releases weights 52. Weights 52 freefall down guide rod 56 until weights 52 reach stop collar 58. Stop collar 58 arrests the freefall of weights 52, causing an impulse load to be transmitted to loading member 24 through guide rod 56.

One simple use of the proposed testing apparatus and method involves determining how much of an impact load is needed for the material to fail. Those that are skilled in the art know that the size of the impact load is a function of the total weight of the masses and the distance over which the masses fall before contacting stop collar 58. The tester may design a simple experiment which tests different weights and falling distances to determine the minimum impact load required for material failure.

The testing device can also be configured to test specimens of the same or similar configuration as that specified in the standardized testing method ASTM D638. An illustration of the testing device in such a configuration is provided in FIG. 8. Test sample 72 represents a test specimen commonly used in the standardized testing method ASTM D638. Test sample 72 has two end portions and a narrowed midsection running therebetween. One end is attached to the testing device by clamp 74. Clamp 74 may be any type of clamp. In the present illustration, clamp 74 is attached to one end portion of test sample 72 by a hex bolt which passes through clamp 74 and the end portion of test sample 72. Clamp 76 is similarly attached to the other end portion of test sample 72. Clamp 76 includes rod receiver 78. Rod receiver 78 has female thread which is configured to engage the male thread of guide rod 56. Guide rod 56 also passes through weights 52, brace 84 and stop plate 80. Stop plate 80 is provided to arrest the free fall of guide rod 56 if test sample 72 breaks. Dampers 82 are provide between stop plate 80 and brace 84 to reduce the impact on the components of the testing fixture when rod receiver 78 falls into stop plate 80.

Figure 8:
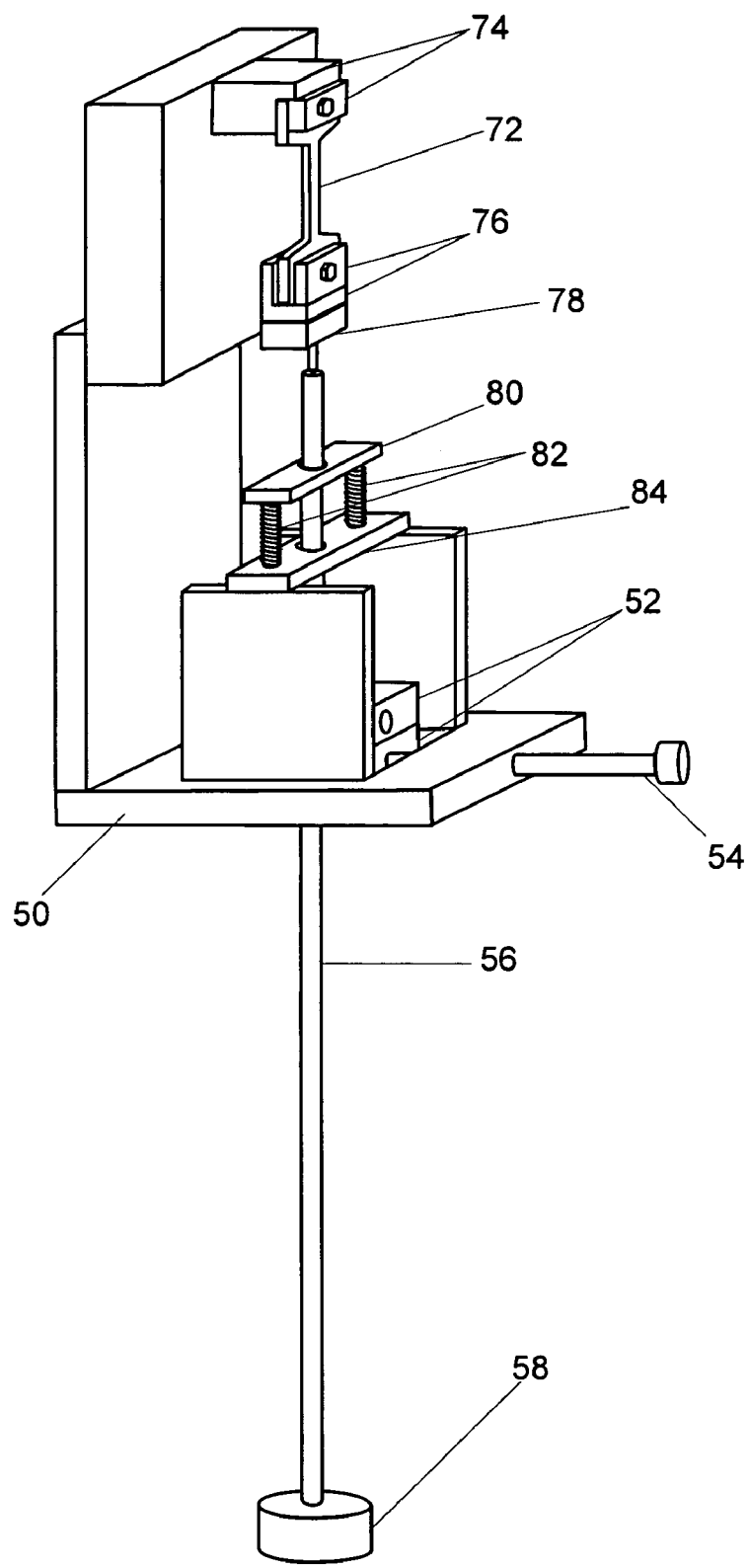
FIG. 8 is a perspective view, showing a testing fixture.

The testing device illustrated in FIG. 8 allows the user to correlate his or her test results with a wide variety of other test results for both base materials and component properties. For example, measured properties of a section of pipe can be compared to plaque samples comprised of the same material. This will provide important insights of the effect of pipe geometry and manufacturing processes on the properties of the actual pipe. Similarly, results obtained using the proposed testing device can be correlated with such properties as tensile strength and crack resistance.

The preceding description contains significant detail regarding the novel aspects of the present invention. It should not be construed, however, as limiting the scope of the invention but rather as providing illustrations of the preferred embodiments of the invention. As an example, vertical clamp 36 need not be a screw clamp. Other types of clamps may also be used. Such variations would not alter the function of the invention. Thus, the scope of the invention should be fixed by the following claims, rather than by the examples given.

We claim:

1. A testing fixture for evaluating the effect of an impact load on a test sample, said test sample having a clamped portion, a loading member extending therefrom, and a bore passing through said loading member, said clamped portion having a first sidewall member, a second sidewall member, and a trough positioned therebetween, said testing fixture comprising:
   a. a vertical clamp configured to clamp said clamped portion of said test sample in a stationary position so that said loading member projects outwardly away from said vertical clamp;
   b. a guide rod, having a first end, a second end and a medial section therebetween, said first end of said guide rod configured to attach to said bore in said loading member;
   c. a mass slidably situated on said guide rod, said mass configured to slide a fixed distance along said guide rod from a first position proximal said medial section of said guide rod to a second position proximal said second end of said guide rod;
   d. a plunger, said plunger movable between a third position and a fourth position, wherein when said plunger is positioned in said third position, said plunger is configured to mechanically engage and hold said mass in said first position, and when said plunger is positioned in said fourth position, said plunger is configured to disengage and release said mass so that said mass falls from said first position to said second position;
   e. a stop collar attached to said guide rod proximal said second end of said guide rod, configured to stop said mass at said second position causing said impact load to be transmitted along said guide rod to said loading member.

2. The testing fixture of claim 1, said vertical clamp further comprising a clamp face, said clamp face configured to mate with said trough of said test sample when said clamped portion of said test sample is clamped by said vertical clamp.

3. The testing fixture of claim 2, said clamp face further comprising a first sidewall mating surface and a second sidewall mating surface, wherein said first sidewall mating surface is configured to mate with said first sidewall member of test sample when said test sample is clamped by said vertical clamp, and wherein said second sidewall mating surface is configured to mate with said second sidewall member of said test sample when said test sample is clamped by said vertical clamp.

4. The testing fixture of claim 1, further comprising a knob, said knob configured to attach to said first end of said guide rod so as to attach said guide rod to said loading member when said first end of said guide rod is inserted through said bore of said loading member and said knob is attached to said first end of said guide rod.

5. The testing fixture of claim 4, wherein said first end of said guide rod has a male thread and said knob has a female thread configured to engage said male thread of said guide rod.

6. The testing fixture of claim 1, wherein said stop collar is adjustably fastened to said guide rod so that said stop collar may be moved and fastened to a different position along said medial section of said guide rod.

7. A method for testing the effect of an impact load on a corrugated pipe comprising the steps of:
   a. preparing a test sample, wherein said step of preparing said test sample includes the steps of
      i. obtaining a section of said corrugated pipe;
      ii. cutting said test sample from said section such that said test sample has a clamped portion and a loading member extending outwardly therefrom;
      iii. boring a hole through said loading member;
   b. obtaining a testing fixture, said testing fixture having
      i. a vertical clamp configured to retain said clamped portion of said test sample in a stationary position but allow said loading member to be free to move;
      ii. a guide rod, having a first end, a second end and a medial section therebetween, said guide rod attachable to said hole of said loading member proximal said first end;
      iii. a mass slidably situated on said guide rod, said mass configured to slide a fixed distance along said guide rod from a first position proximal said medial section of said guide rod to a second position proximal said second end of said guide rod;
   c. clamping said clamped portion of said test sample in said vertical clamp such that said clamped portion of said test sample is retained in a stationary position but said loading member is free to move;
   d. attaching said guide rod to said loading member; and
   e. loading said loading member with said impact load by allowing said mass to fall to said second position.

8. The method of claim 7, said testing fixture further comprising a plunger, said plunger movable between a third position and a fourth position, wherein when said plunger is positioned in said third position, said plunger is configured to hold said mass in said first position, and when said plunger is positioned in said fourth position, said mass is released so that said mass falls from said first position to said second position.

9. The method of claim 7, said testing fixture further comprising a stop collar proximal said second end of said guide rod, configured to stop said mass at said second position causing said impact load to be transmitted to said loading member.

10. The method of claim 9, wherein said stop collar is adjustably fastened to said guide rod so that said stop collar may be moved and fastened to a different position along said medial section of said guide rod.

11. The method of claim 7, wherein said vertical clamp of said testing fixture further comprising a clamp face, said clamp face configured to mate with said trough of said test sample when said clamped portion of said test sample is clamped by said vertical clamp.

12. The method of claim 7, wherein said test sample is prepared to have said clamped portion having a first sidewall member, a second sidewall member, and a trough positioned therebetween.

13. The method of claim 12, said clamp face of said testing fixture further comprising a first sidewall mating surface and a second sidewall mating surface, wherein said first sidewall mating surface is configured to mate with said first sidewall member of test sample when said test sample is clamped by said vertical clamp, and wherein said second sidewall mating surface is configured to mate with said second sidewall member of said test sample when said test sample is clamped by said vertical clamp.

14. The method of claim 7, said testing fixture further comprising a knob, said knob configured to attach to said first end of said guide rod so as to attach said guide rod to said loading member when said first end of said guide rod is inserted through said bore of said loading member and said knob is attached to said first end of said guide rod.

15. The method of claim 14, wherein said first end of said guide rod has a male thread and said knob has a female thread configured to engage said male thread of said guide rod.

* * * * *